United States Patent [19]

Henry

[11] 4,175,548

[45] Nov. 27, 1979

[54] MASSAGE BACK BRACE

[75] Inventor: Robert J. Henry, Kelso, Wash.

[73] Assignee: Harry A. Wood, Longview, Wash.; a part interest

[21] Appl. No.: 829,197

[22] Filed: Aug. 30, 1977

[51] Int. Cl.$^2$ .......................... A61H 1/00; A61F 5/02

[52] U.S. Cl. ...................................... 128/24 R; 128/78

[58] Field of Search ................ 128/78, 24 R, 96; 2/44

[56] References Cited

U.S. PATENT DOCUMENTS

| | | | |
|---|---|---|---|
| 3,856 | 12/1844 | Cutter | 128/96 X |
| 1,940,904 | 12/1933 | Dayton et al. | 128/78 |
| 2,320,183 | 5/1943 | Jungmann | 128/78 |
| 2,733,712 | 2/1956 | Wuesthoff | 128/78 |
| 3,154,072 | 10/1964 | Mack | 128/78 |

FOREIGN PATENT DOCUMENTS

| | | | |
|---|---|---|---|
| 106 | 10/1885 | Sweden | 128/96 |
| 480415 | 11/1975 | U.S.S.R. | 128/24 R |

*Primary Examiner*—Lawrence W. Trapp
*Attorney, Agent, or Firm*—Clarence O'Brien; Harvey B. Jacobson

[57] ABSTRACT

A massage back brace having a resilient arrangement mounted on a flexible support member and covered by a resilient pad. The brace is affixable in position on a wearer's back by a belt-like strap removably attachable to the flexible support member and fastened together about a wearer's torso.

9 Claims, 3 Drawing Figures

MASSAGE BACK BRACE

BACKGROUND OF THE INVENTION

1. Field of the Invention

This invention relates generally to an orthopedic appliance, and particularly to a massage back brace for relieving backaches, and the like, of a user during sleeping, long automobile trips, and other periods in which a prolonged lying or sitting position is maintained.

2. Description of the Prior Art

Many people are affected by what is sometimes referred to as "morning backaches" wherein pain occurs in the lumbar area of one's back, especially after sleeping or driving long distances. While various braces have been proposed for relieving this pain, such braces are either of little value for the purpose, and/or are extremely uncomfortable to wear while one is walking, driving, sleeping, and the like.

As a result of the aforementioned difficulties, people who suffer from pain in the lumbar area of their back are somewhat limited in their activities, and particularly find it difficult to be active in the early morning hours after awakening from a poor night's sleep with a backache.

SUMMARY OF THE INVENTION

It is an object of the present invention to provide a back brace which massages the back as the user's torso moves relative to the brace.

It is another object of the present invention to provide a back brace which functions in the manner of an orthopedic mattress so as to massage the user's back during movement of the user's torso.

It is yet another object of the present invention to provide a back brace which is comfortable to wear, and can be worn virtually continuously without discomfort and annoyance to the wearer.

These and other objects are achieved according to the present invention by providing a back brace having: a support member; a resilient arrangement mounted on the support member for massaging the back, or lumbar, area of a wearer of the brace; and a cover assembly arranged over the resilient arrangement for covering the resilient arrangement.

A flexible strap advantageously is removably attachable to the support member on a surface thereof spaced from the resilient arrangement for mounting the brace on the back portion of a human torso. This flexible strap can be fastened together at the ends thereof as by a suitable fastener.

The resilient arrangement includes a pair of assemblies each comprising a strip of self-supporting sheet material, such as a sheet metal, having a face from which extend codirectionally a plurality of coiled compression springs mounted in spaced relation about the face of the strip. The cover assembly preferably includes a pad constructed from a resilient material, such as a foamed rubber and the like, disposed for embedding the resilient assemblies so as to protect the user's skin from the coiled springs. Partially enclosing this pad, and entirely covering the flexible support member, can be disposed a fabric cover, constructed from cloth, nylon, and the like, held together by a drawstring threaded through a loop extending continuously around an opening provided in the cover. This cover will protect the user and a bed, car seat, and the like, as well as the user's clothing, from damage due to rivets or other suitable fasteners employed in conjunction with the attachment of the resilient assemblies to the support member.

These, together with other objects and advantages which will become subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
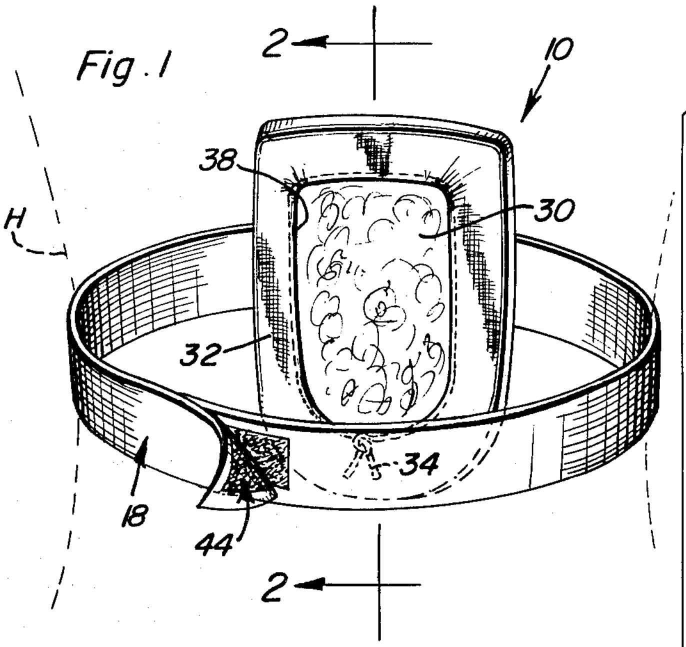
FIG. 1 is a perspective view showing a back brace according to the invention as it would appear strapped onto a user's body.
Figure 2:
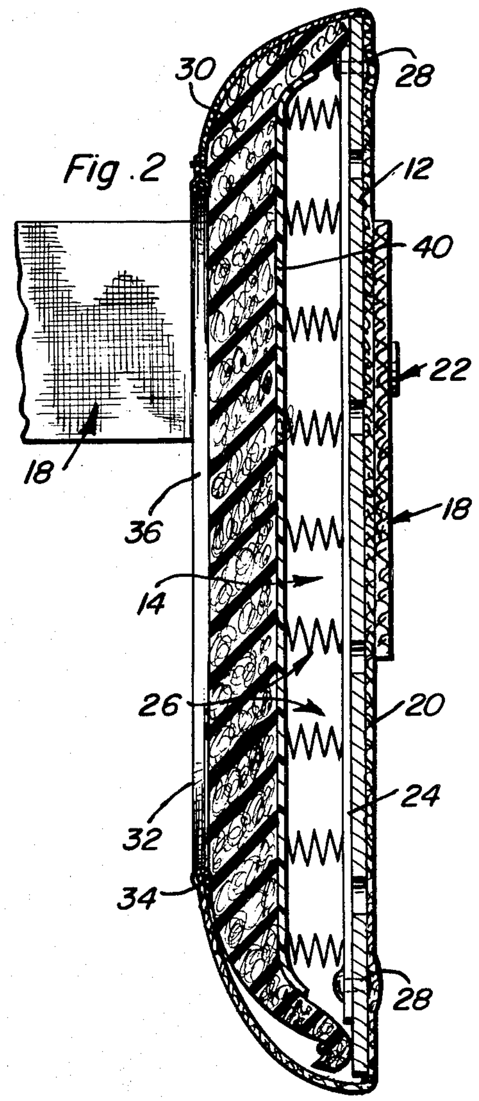
FIG. 2 is an enlarged, fragmentary, sectional view taken generally along the line 2—2 of FIG. 1.
Figure 3:
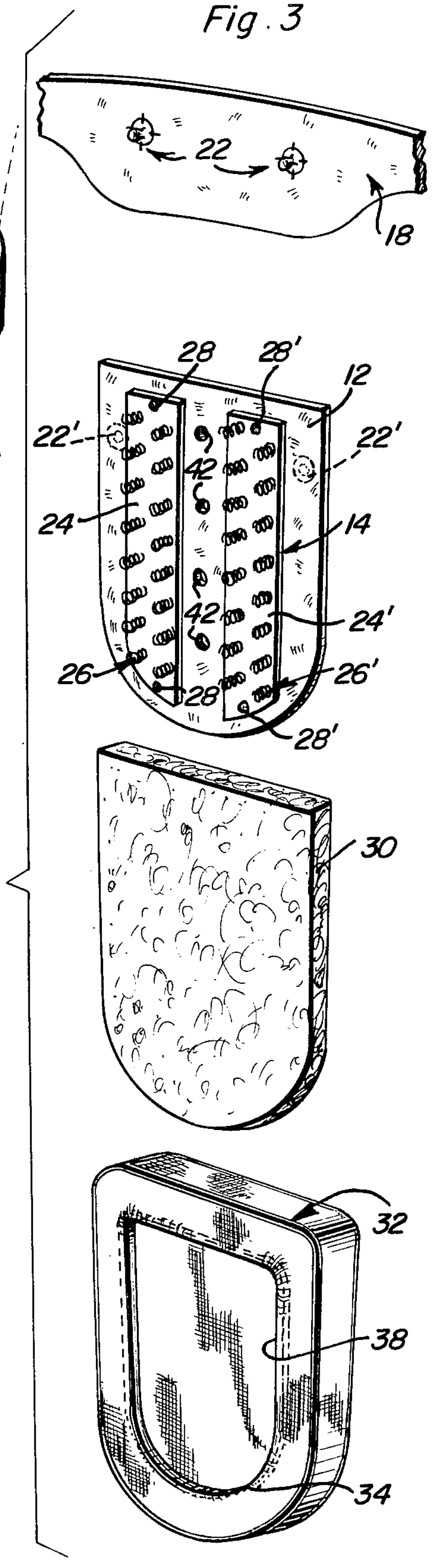
FIG. 3 is an exploded, fragmentary, perspective view showing the various elements forming a back brace according to the present invention and as seen in FIGS. 1 and 2.

Referring now more particularly to the Figures of the drawing, a massage back brace 10 according to the present invention includes a flexible support member 12 on which is mounted a resilient arrangment 14. Arranged over arrangement 14 is a cover assembly 16 for covering the arrangement 14. Support member 12 can be, for example, a 4–9 ounce piece of leather, and the like, which is essentially stiffened by the resilient arrangement 14. The latter functions to massage the back, for example, of a user during movement of the user's body.

A flexible strap 18, preferably constructed from a suitable, known 4-way stretch material, is removably attachable to support member 12 on a surface 20 thereof as by the conventional snap fasteners 22 and 22' for permitting the brace to be mounted on the back portion of a human torso H.

The resilient arrangement 14 includes a pair of assemblies each comprising a strip 24, 24' of self-supporting sheet material, such as sheet metal, having a face on which are mounted a plurality of codirectionally extending, coiled compression springs 26, 26' disposed in spaced relation about the face of the associated strip 24, 24'. Suitable rivets 28, 28' can be used to attach the strips 24, 24', respectively, to flexible support member 12 so that the strips 24, 24' are arranged in spaced side-by-side relation on support member 12 for stiffening same as well as for mounting the springs 26, 26' on support member 12.

Springs 26, 26' can be attached at a one end thereof to an associated strip 24, 24' in a conventional manner, such as by brazing, but preferably the spring ends are inserted into slots made in the stips 24, 24' as by a punching operation which forms an "T" in the metal. By known tooling techniques, all of the holes in a strip 24, 24' can be punched in one operation, including the holes for rivets 28, 28', and the strips simultaneously cut to proper length and shape. Subsequently to insertion of the spring ends, the metal could be punched back down on the end of the springs for retaining same, and to assure retention, the spring end could even be brazed or welded in place.

Cover assembly 16 includes a pad 30 of resilient material, such as a suitable foamed synthetic or natural rubber, disposed embedding the springs 27, 26' of resilient arrangement 14. A cover 32 constructed from a flexible material, such as a fabric made from cotton, nylon, and the like, can be arranged partially encasing the support member 12, resilient arrangement 14, and pad 30 so as to form a protective covering for the brace 10. More specifically, cover 32 has a drawstring 34 arranged extending through in slidable fashion a loop 36 formed almost continuously around the periphery of the material forming cover 32. Tightening of string 34 will cause cover 32 to conform tightly to the configuration of support member 12 and pad 30, and will retain cover 32 in proper position. Simultaneously, since the drawstring 34 will not completely close cover 32 on itself, an opening 38 will be formed adjacent the pad 30. By this arangement, the surface 20 of support member 12, as well as the heads of rivets 28, 28' provided therein, are covered so as to protect the user's person, the user's clothing, and articles of furniture, and the like, which the user may contact from damage from the support member and rivets. In addition, a piece of material, such as a suitable fabric, can be, for example, stitched onto support member 12 so as to cover the surface 20 thereof in a manner not shown.

A sheet of suitable synthetic material, and the like, can be employed as a backing sheet 40 disposed between springs 26, 26' and the surface of pad 30 abutting the outward ends of the springs 26, 26', while rivets, and the like, can be employed to form a plurality of vents 42 extending from top to bottom of support member 12 in the space provided between the strips 24 and 24'.

While the ends of strap 18 can be fastened in any convention manner, the preferred mode of attachment is to use a conventional hook fastener 44, such as those fasteners sold under the registered trademark "VELCRO".

In operation, brace 10 can be attached to a 4-way stretch belt, or sacrum belt, forming strap 18, and the brace secured to the person's body, or brace 10 can be employed without a strap 18 merely by slipping the brace inside the user's clothing. The vents 42 will permit the leather from which support member 12 is constructed to breathe while brace 10 is being worn. While any suitable material can be used for the strips 24, 24', stainless steel has been found preferable in order to obtain the desired elasticity and stiffness of the strips 24, 24'. Springs 26, 26' will act like invisible fingers massaging the wearer's back, whether the wearer is walking or moving about on a seat, or sleeping on the brace 10, or however the appliance is being worn.

The brace 10 can be unhooked from the strap 18 at night, and the brace merely placed in the small of the user's back, that being the lumbar area, and the user can then sleep on the brace in comfort. As the user moves or rolls during sleep, the series of springs 26, 26' massages the user's back. The cover 32 is made readily removable for washing and for permitting cleaning of the pad 30.

As can be readily understood from the above description from the drawings, a massage back brace according to the present invention provides relief from those suffering with lumbar pains in a comfortable and safe manner, and permits people suffering from such pains to enjoy a full range of activity, even in the early morning hours.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A massage back brace, comprising, in combination:
(a) a support member;
(b) resilient means mounted on the support member for massaging the back of a user of the brace including a strip of self-supporting sheet material having a face, and a plurality of codirectionally extending, coiled compression springs mounted in spaced relation about the face of the strip; and
(c) cover means arranged over the resilient means for covering the resilient means.

2. A structure as defined in claim 1, wherein the support member is constructed from a sheet of flexible material, and the resilient means includes a pair of the strips and associated springs, each of the strips and associated springs being substantially like the other and disposed in spaced side-by-side relation on the support member for stiffening same.

3. A structure as defined in claim 1, wherein the cover means includes a pad of resilient material disposed embedding the resilient means.

4. A structure as defined in claim 3, wherein the cover means further includes a cover of flexible material arranged encasing the support member and resilient means, and partially covering the pad.

5. A structure as defined in claim 4, further including a flexible strap means removably attached to the support member on a surface thereof spaced from the resilient means for mounting the brace on the back portion of a human torso.

6. A massage back brace, comprising, in combination:
(a) a support member;
(b) resilient means mounted on the support member for massaging the back of a user of the brace; and
(c) cover means arranged over the resilient means for covering the resilient means including a pad of resilient material disposed embedding the resilient means.

7. A structure as defined in claim 6, wherein the cover means further includes a cover of flexible material arranged encasing the support member and resilient means, and partially covering the pad.

8. A structure as defined in claim 1, further including a flexible strap means removably attached to the support member on a surface thereof spaced from the resilient means for mounting the brace on the back portion of a human torso.

9. A resilient arrangement for a massage back brace, comprising, in combination:
(a) a strip of self-supporting sheet material having a face; and
(b) a plurality of codirectionally extending, coiled compression springs mounted in spaced relation about the face of the strip for massaging a human back with which the resilient arrangement abuts.

* * * * *